(12) United States Patent
Landry et al.

(10) Patent No.: US 9,398,957 B2
(45) Date of Patent: Jul. 26, 2016

(54) FEMORAL AND TIBIAL BASES

(71) Applicant: MOXIMED, INC., Hayward, CA (US)

(72) Inventors: Michael E. Landry, Austin, TX (US); Anton G. Clifford, Mountain View, CA (US); Ezra T. Schiff, Mountain View, CA (US)

(73) Assignee: MOXIMED, INC., Hayward, CA (US)

( * ) Notice: Subject to any disclaimer, the term of this patent is extended or adjusted under 35 U.S.C. 154(b) by 0 days.

(21) Appl. No.: 14/183,047

(22) Filed: Feb. 18, 2014

(65) Prior Publication Data

US 2014/0188234 A1 Jul. 3, 2014

Related U.S. Application Data

(60) Division of application No. 12/755,335, filed on Apr. 6, 2010, now abandoned, and a continuation-in-part of application No. 12/112,442, filed on Apr. 30, 2008, now abandoned, which is a continuation-in-part of (Continued)

(51) Int. Cl.
*A61F 2/38* (2006.01)
*A61B 17/56* (2006.01)

(52) U.S. Cl.
CPC .............. *A61F 2/3836* (2013.01); *A61B 17/56* (2013.01); *A61B 2017/567* (2013.01)

(58) Field of Classification Search
CPC .............. A61F 2/3836; A61B 17/562; A61B 2017/567
See application file for complete search history.

(56) References Cited

U.S. PATENT DOCUMENTS

| 2,632,440 | A | 3/1953 | Hauser |
| 2,877,033 | A | 3/1959 | Koetke |
| 3,242,922 | A | 3/1966 | Thomas |
| 3,648,294 | A | 3/1972 | Shahrestani |
| 3,681,786 | A | 8/1972 | Lynch |
| 3,779,654 | A | 12/1973 | Horne |
| 3,875,594 | A | 4/1975 | Swanson |
| 3,902,482 | A | 9/1975 | Taylor |
| 3,988,783 | A | 11/1976 | Treace |

(Continued)

FOREIGN PATENT DOCUMENTS

| CA | 1205602 | 6/1986 |
| DE | 19855254 | 6/2000 |

(Continued)

OTHER PUBLICATIONS

PCT search report dated Jan. 20, 2010 from PCT application No. PCT/US2009/002714 as issued by the European Patent Office as searching authority.

(Continued)

*Primary Examiner* — Brian Dukert
(74) *Attorney, Agent, or Firm* — Adam J. Cermak; Cermak Nakajima & McGowan LLP

(57) ABSTRACT

Various embodiments are directed to femoral and tibial bases that form structures of an implantable mechanical energy absorbing system. According to one embodiment, the bases include a low-profile body having a elongate and a curved body portion. One end of the base is elevated as compared to another end. An inner surface of the low-profile body has a raised portion extending along the elongate, straight portion of the low-profile body. The bases also include a plurality of openings positioned along the low-profile body for alignment and purposes of affixation to body anatomy.

12 Claims, 8 Drawing Sheets

Related U.S. Application Data application No. 11/743,097, filed on May 1, 2007, and a continuation-in-part of application No. 11/743,605, filed on May 2, 2007, and a continuation-in-part of application No. 11/775,139, filed on Jul. 9, 2007, now Pat. No. 7,611,540, and a continuation-in-part of application No. 11/775,149, filed on Jul. 9, 2007, now Pat. No. 7,655,041, and a continuation-in-part of application No. 11/775,145, filed on Jul. 9, 2007, now Pat. No. 7,678,147.

(56) References Cited

U.S. PATENT DOCUMENTS

| | | | |
|---|---|---|---|
| 4,187,841 A | 2/1980 | Knutson | |
| 4,246,660 A | 1/1981 | Wevers | |
| 4,308,863 A | 1/1982 | Fischer | |
| 4,353,361 A | 10/1982 | Foster | |
| 4,501,266 A | 2/1985 | McDaniel | |
| 4,570,625 A | 2/1986 | Harris | |
| 4,576,158 A | 3/1986 | Boland | |
| 4,621,627 A | 11/1986 | DeBastiani et al. | |
| 4,637,382 A | 1/1987 | Walker | |
| 4,696,293 A | 9/1987 | Ciullo | |
| 4,759,765 A | 7/1988 | Van Kampen | |
| 4,776,851 A | 10/1988 | Bruchman et al. | |
| 4,846,842 A | 7/1989 | Connolly et al. | |
| 4,871,367 A | 10/1989 | Christensen et al. | |
| 4,923,471 A | 5/1990 | Morgan | |
| 4,942,875 A | 7/1990 | Hlavacek et al. | |
| 4,959,065 A | 9/1990 | Arnett et al. | |
| 4,988,349 A | 1/1991 | Pennig | |
| 5,002,574 A | 3/1991 | May et al. | |
| 5,011,497 A | 4/1991 | Persson et al. | |
| 5,019,077 A | 5/1991 | De Bastiani et al. | |
| 5,026,372 A | 6/1991 | Sturtzkopf et al. | |
| 5,041,112 A | 8/1991 | Mingozzi et al. | |
| 5,100,403 A | 3/1992 | Hotchkiss et al. | |
| 5,103,811 A | 4/1992 | Crupi | |
| 5,121,742 A | 6/1992 | Engen | |
| 5,152,280 A | 10/1992 | Danieli | |
| 5,201,881 A | 4/1993 | Evans | |
| 5,318,567 A | 6/1994 | Vichard | |
| 5,352,190 A | 10/1994 | Fischer | |
| 5,375,823 A | 12/1994 | Navas | |
| 5,405,347 A | 4/1995 | Lee et al. | |
| 5,415,661 A | 5/1995 | Holmes | |
| 5,540,688 A | 7/1996 | Navas | |
| 5,575,819 A | 11/1996 | Amis | |
| 5,578,038 A | 11/1996 | Slocum | |
| 5,601,553 A | 2/1997 | Trebling et al. | |
| 5,624,440 A | 4/1997 | Huebner | |
| 5,662,648 A | 9/1997 | Faccioli et al. | |
| 5,662,650 A | 9/1997 | Bailey et al. | |
| 5,681,313 A | 10/1997 | Diez | |
| 5,695,496 A | 12/1997 | Orsak et al. | |
| 5,716,357 A | 2/1998 | Rogozinski | |
| 5,803,924 A | 9/1998 | Oni et al. | |
| 5,873,843 A | 2/1999 | Draper | |
| 5,928,234 A | 7/1999 | Manspeizer | |
| 5,976,125 A | 11/1999 | Graham | |
| 5,976,136 A | 11/1999 | Bailey et al. | |
| 5,993,449 A | 11/1999 | Schlapfer | |
| 6,036,691 A | 3/2000 | Richardson | |
| 6,113,637 A | 9/2000 | Gill et al. | |
| 6,139,550 A | 10/2000 | Michelson | |
| 6,162,223 A | 12/2000 | Orsak et al. | |
| 6,176,860 B1 | 1/2001 | Howard | |
| 6,264,696 B1 | 7/2001 | Reigner et al. | |
| 6,277,124 B1 | 8/2001 | Haag | |
| 6,315,852 B1 | 11/2001 | Magrini et al. | |
| 6,355,037 B1 | 3/2002 | Crosslin et al. | |
| 6,364,881 B1 | 4/2002 | Apgar et al. | |
| 6,409,729 B1 | 6/2002 | Martinelli et al. | |
| 6,482,232 B1 | 11/2002 | Boucher et al. | |
| 6,494,914 B2 | 12/2002 | Brown et al. | |
| 6,527,733 B1 | 3/2003 | Ceriani et al. | |
| 6,540,708 B1 | 4/2003 | Manspeizer | |
| 6,572,653 B1 | 6/2003 | Simonson | |
| 6,599,322 B1 | 7/2003 | Amrich et al. | |
| 6,620,332 B2 | 9/2003 | Amrich | |
| 6,623,486 B1 | 9/2003 | Weaver et al. | |
| 6,663,631 B2 | 12/2003 | Kuntz | |
| 6,692,497 B1 | 2/2004 | Tormala et al. | |
| 6,692,498 B1 | 2/2004 | Niiranen et al. | |
| 6,752,831 B2 | 6/2004 | Sybert et al. | |
| 6,884,242 B2 | 4/2005 | LeHuec et al. | |
| 6,966,910 B2 | 11/2005 | Ritland | |
| 6,972,020 B1 | 12/2005 | Grayson et al. | |
| 6,997,940 B2 | 2/2006 | Bonutti | |
| 7,018,418 B2 | 3/2006 | Amrich et al. | |
| 7,029,475 B2 | 4/2006 | Panjabi | |
| 7,128,744 B2 | 10/2006 | Weaver et al. | |
| 7,141,073 B2 | 11/2006 | May et al. | |
| 7,188,626 B2 | 3/2007 | Foley et al. | |
| 7,201,728 B2 | 4/2007 | Sterling | |
| 7,235,077 B1 | 6/2007 | Wang et al. | |
| 7,235,102 B2 | 6/2007 | Ferree et al. | |
| 7,238,203 B2 | 7/2007 | Bagga et al. | |
| 7,241,298 B2 | 7/2007 | Nemec et al. | |
| 7,247,157 B2 | 7/2007 | Prager et al. | |
| 7,252,670 B2 | 8/2007 | Morrison et al. | |
| 7,261,739 B2 | 8/2007 | Ralph et al. | |
| 7,273,481 B2 | 9/2007 | Lombardo et al. | |
| 7,276,070 B2 | 10/2007 | Muckter | |
| 7,282,065 B2 | 10/2007 | Kirschman | |
| 7,285,134 B2 | 10/2007 | Berry et al. | |
| 7,288,094 B2 | 10/2007 | Lindemann et al. | |
| 7,288,095 B2 | 10/2007 | Baynham et al. | |
| 7,291,150 B2 | 11/2007 | Graf | |
| 7,306,605 B2 | 12/2007 | Ross | |
| 7,322,983 B2 | 1/2008 | Harris | |
| 7,322,984 B2 | 1/2008 | Doubler et al. | |
| 7,341,589 B2 | 3/2008 | Weaver et al. | |
| 7,361,196 B2 | 4/2008 | Fallin et al. | |
| 7,553,331 B2 * | 6/2009 | Manspeizer | A61F 2/3836 606/90 |
| 2001/0020143 A1 | 9/2001 | Stark et al. | |
| 2002/0095154 A1 | 7/2002 | Atkinson et al. | |
| 2002/0151975 A1 | 10/2002 | Farr, II et al. | |
| 2002/0151978 A1 | 10/2002 | Zacouto et al. | |
| 2003/0040749 A1 | 2/2003 | Grabowski et al. | |
| 2003/0216809 A1 | 11/2003 | Ferguson | |
| 2004/0102778 A1 | 5/2004 | Huebner et al. | |
| 2004/0260302 A1 | 12/2004 | Manspeizer | |
| 2004/0267179 A1 | 12/2004 | Leman | |
| 2005/0049708 A1 | 3/2005 | Atkinson et al. | |
| 2005/0085815 A1 | 4/2005 | Harms et al. | |
| 2005/0119744 A1 | 6/2005 | Buskirk et al. | |
| 2005/0154390 A1 | 7/2005 | Biedermann et al. | |
| 2005/0192674 A1 | 9/2005 | Ferree | |
| 2005/0261680 A1 | 11/2005 | Draper | |
| 2006/0064169 A1 | 3/2006 | Ferree | |
| 2006/0085001 A1 | 4/2006 | Michelson | |
| 2006/0178744 A1 | 8/2006 | de Villiers et al. | |
| 2007/0043356 A1 | 2/2007 | Timm et al. | |
| 2007/0106299 A1 | 5/2007 | Manspeizer | |
| 2007/0161993 A1 | 7/2007 | Lowery et al. | |
| 2007/0168033 A1 | 7/2007 | Kim et al. | |
| 2007/0168036 A1 | 7/2007 | Ainsworth et al. | |
| 2007/0198088 A1 | 8/2007 | Biedermann et al. | |
| 2007/0198091 A1 | 8/2007 | Boyer et al. | |
| 2007/0244483 A9 | 10/2007 | Winslow et al. | |
| 2007/0244488 A1 | 10/2007 | Metzger et al. | |
| 2007/0288014 A1 | 12/2007 | Shadduck et al. | |
| 2008/0015591 A1 | 1/2008 | Castaneda et al. | |
| 2008/0015592 A1 | 1/2008 | Long et al. | |
| 2008/0015593 A1 | 1/2008 | Pfefferle et al. | |
| 2008/0071373 A1 | 3/2008 | Molz et al. | |
| 2008/0071375 A1 | 3/2008 | Carver et al. | |
| 2008/0097441 A1 | 4/2008 | Hayes et al. | |
| 2008/0132954 A1 | 6/2008 | Sekhon et al. | |
| 2008/0154378 A1 | 6/2008 | Pelo | |
| 2008/0275560 A1 | 11/2008 | Clifford et al. | |

(56) References Cited

U.S. PATENT DOCUMENTS

| | | |
|---|---|---|
| 2009/0043310 A1 | 2/2009 | Rasmussen |
| 2009/0275947 A1 | 11/2009 | Graham et al. |
| 2009/0276054 A1 | 11/2009 | Clifford et al. |
| 2012/0123551 A1 | 5/2012 | Landry et al. |

FOREIGN PATENT DOCUMENTS

| | | |
|---|---|---|
| EP | 0383419 | 8/1990 |
| EP | 0953317 | 4/1999 |
| EP | 1770302 | 4/2007 |
| EP | 1429675 | 10/2007 |
| EP | 1682020 | 10/2007 |
| EP | 1847228 | 10/2007 |
| EP | 1847229 | 10/2007 |
| EP | 1005290 | 2/2008 |
| EP | 1468655 | 5/2008 |
| GB | 1507953 | 4/1978 |
| GB | 2223406 | 4/1990 |
| GB | 2250919 | 5/1991 |
| GB | 2250919 | 10/1993 |
| JP | 59-131348 | 7/1984 |
| JP | 2532346 | 4/1995 |
| JP | 7100159 | 4/1995 |
| JP | 2000-503865 | 4/2000 |
| JP | 2001-145647 | 4/2000 |
| JP | 2003-102744 | 5/2001 |
| JP | 2006-280951 | 10/2006 |
| JP | 2007-167318 | 7/2007 |
| JP | 2007-167319 | 7/2007 |
| JP | 2007170969 | 7/2007 |
| RU | 1769868 | 10/1992 |
| RU | 2085148 | 7/1997 |
| RU | 2217105 | 11/2003 |
| RU | 2241400 | 9/2004 |
| SU | 578063 | 11/1977 |
| SU | 578957 | 11/1977 |
| SU | 624613 | 8/1978 |
| SU | 640740 | 1/1979 |
| SU | 704605 | 12/1979 |
| SU | 719612 | 3/1980 |
| SU | 741872 | 7/1980 |
| SU | 1186204 | 10/1985 |
| SU | 1251889 | 8/1986 |
| SU | 1316666 | 6/1987 |
| SU | 1588404 | 8/1990 |
| SU | 1699441 | 12/1991 |
| WO | WO9107137 | 5/1991 |
| WO | WO94/06364 | 3/1994 |
| WO | WO 94/08384 | 3/1994 |
| WO | WO96/19944 | 7/1996 |
| WO | WO 96/19944 | 7/1996 |
| WO | WO2004/019831 | 3/2004 |
| WO | WO2004/024037 | 3/2004 |
| WO | WO 2004019831 | 3/2004 |
| WO | WO 2004024037 | 3/2004 |
| WO | WO2007/056645 | 5/2005 |
| WO | WO 2007058845 | 5/2005 |
| WO | WO2006045091 | 4/2006 |
| WO | WO2006049993 | 5/2006 |
| WO | WO2006/110578 | 10/2006 |
| WO | WO 2006110578 | 10/2006 |
| WO | WO2007/090009 | 8/2007 |
| WO | WO2007/090015 | 8/2007 |
| WO | WO2007/090017 | 8/2007 |
| WO | WO 2007030003 | 8/2007 |
| WO | WO 2007030015 | 8/2007 |
| WO | WO 2007030017 | 8/2007 |
| WO | WO2007106962 | 9/2007 |
| WO | WO 2007108438 | 9/2007 |
| WO | WO 2007108962 | 9/2007 |
| WO | WO2007109417 | 9/2007 |
| WO | WO 2007109417 | 9/2007 |
| WO | WO2007109436 | 9/2007 |
| WO | WO2007114769 | 10/2007 |
| WO | WO 2007114769 | 10/2007 |
| WO | WO2007117571 | 10/2007 |
| WO | WO 2007117571 | 10/2007 |
| WO | WO2008006098 | 1/2008 |
| WO | WO 2008008098 | 1/2008 |
| WO | WO2008/137487 | 11/2008 |

OTHER PUBLICATIONS

Lapinskaya, Valentina Spiridovna, "Treatment of Diseases and Injuries of Hip Joint Using a Method of Distractions", Kuibyshev Medial Institute, 1990.

Lanonov d. Yu, et al., "Medical Devices", Scientific and Technical Bimonthly Journal, May-Jun. 2008.

Lapinskaya, V.S., et al., "An Endoapparatus for Restoration of the Hip Joint", Writers Collective, 2008, UDK 615.472.03:616,728.2-089.28.

Nagai, et al., "B109 Mobility Evaluation of Hip-Joint Nonweight-Bearing Device", The Japan Society of Mechanical Engineers No. 02-26.

Tomita, Naohide, "Development of Treatment Devices for Cartilage Regeneration", BME vol. 16, No. 2.

Lentsner, A.A., et al., "Device for Functional Relief of Hip Joint in Cotyloid Cavity Fracture Cases", Ortop Travmatol Protez. Apr. 1990 (4)44-6.

Wilke, hans-Joachim et al., "Biomechanical Evaluation of a New Total Posterior-Element Replacement System"; Spine, 2006, vol. 31, No. 24, pp. 2790-2796.

Wilkins, Ross M., M.D. et al.; "The Phenix Expandable Prosthesis"; Clinical Orthopaedics and Related Research, No. 382, pp. 51-58.

Yamamoto, Ei et al.; "Effects of Stress Shielding on the Transverse Mechanical Properties of Rabbit Patellar Tendons"; Journal of Biomechanical Engineering, 2000, vol. 122, pp. 608-614.

Aldegheri, Roberto, M.D. et al.; "Articulated Distraction of the Hip—Conservative Surgery for Arthritis in Young Patients", Clinical Orthopaedics and Related Research, No. 301, pp. 94-101.

Benzel, Edward; "Qualititive Attributes of Spinal Implants"; in: Biomechanics of Spine Stabilization, 1995.

Buckwalter, Joseph A,: "Joint distraction for osteoarthritis"; The Lancet, Department of Orthopaedic Surgery, University of Iowa Hospitals and Clinics, vol. 347, Feb. 3, 1996, pp. 279-280.

Coathup, M.J. et al.; "Osseo-mechanical induction of extro-cortiacal plates with references to their surfact properties and goemoetic designs", Elsevier, Biomaterials 20 (1999) 793-800.

Deie, Masataka, M.D. et al.; "A new Articulated Distraction Arthrosplasty Device for Treatment of the Osteoarthritic Knee Joint: A Preliminary Report": Arthroscopy: The Journal of Arthoscopic and Related Surgery; vol. 23, No. 8 (August), 2007: pp. 833-838.

Dienst, M. et al.; "Dynamic external fixation for distal radius fractures"; Clinical Orthopaedics and Related Research, 1997, vol. 338, pp. 160-171.

Gunther, Klaus-Peter, M.D., "Surgical approaches for osteoarthritis"; Best Practice and Research Clinical Rheumatology, vol. 15, No. 4, pp. 627-643, 2001.

Hall, J. et al.; "Use of a hinged external fixations for elbow instability after severe distal humeral fracture"; Journal of Orthopaedic Trauma, 2000, vol. 14, No. 6 pp. 442-448.

Klein, D. et al.; "Percutaneous treatment of carpal, metacarpal, and phalangeal injuries"; Clinical Orthopaedics and Related Research, 200, vol. 375, pp. 116-125.

Krakauer, J. et al.; "Hinged device for fractures involving the proximal interphalangeal joint"; Clinical Orthopaedics and Related Research, 1996, vol. 327, pp. 29-37.

Lafeber et al., Unloading Joints to Treat Osteoarthritis, including Joint Distraction, Current Opinion in Rheumatology 2006, 18; 519-525.

Madey, S. et al; Hinged external fixation of the elbow: optimal axis alignment to minimize motion resistance; Journal of Orthopaedic Trauma, 2000, vol. 14, No. 1, pp. 41-47.

(56) References Cited

OTHER PUBLICATIONS

Neel, Michael D., M.D.; "Repiphysis—Limb Salvage System for the Skeletally Immature"; Wright Medical Techology, Repiphysis Limb Salvage, 2001, pp. 1-8.

Neel, Michael D. M.D. et al.; "Early Multicenter Experience With a Noninvasive Expandable Prosthesis", Clinical Orthopaedics and Related Research, 2003, No. 415, pp. 72-81.

Nockels, Russ P.; "Dynamic Stabilization in the Surgical Management of Painful Lumbar Spinal Disorders"; Spine, 2005, vol. 30, No. 16S, pp. S68-S72.

Perry, Clayton R. et al.; "Patellar Fixation Protected with a Load-Sharing Cable: A Mechanical and Clinical Study": Journal of Orthopaedic Trauma, 1988, vol. 2, No. 3, pp. 234-240.

ORTHOFIX; "Xcaliber Articulated Ankle"; advertising brochure, May 2004.

ORTHOFIX; "Gentle Limb Deformity Correction", website pages, http://www.eight-plate.com/, 2008.

Pilliar et al., Bone ingrowth and Stress Shielding with a Porous Surface Coated Fracture Fixation Plate, Journal of Biomedical Materials Research, vol. 13, 799-810 (1979).

Pollo, Fabian E. et al.; "Reduction of Medical Compartment Loads With Valgus Bracing of the Osteoarthritic Knee"; American Journal Sports Medicine, vol. 30, No. 3, 2002; pp. 414-421.

Repicci, John A., M.D. et al. "Minimally invasive unicondylar knee arthroplasty for the treatment of unicompartmental osteoarthritis: an outpatient bypass procedure"; Orthopaedic Clinics of North America, 35 (2004), pp. 201-216.

Sommerkamp, G. et al.; "Dynamic external fixation of unstable reatures of the distal part of the radius"; The Journal of Bone and Joint Surgery; 1994, vol. 76-A, No. 8, pp. 1149-1161.

Tencer, Allan F. et al. "Fixation of the Patell (Chap, 9.3)"; in: Biomechanics in Orthopedic Trauma Bone Fracture and Fixation, 1994.

Thakur, A.J.; "Tension Band Wiring"; in; The Elements of Fracture Fixation 1997.

Uchikura, C. et al.; "Comparative study of nonbridging and bridging external fixators for unstable distal radius fractures"; Journal of Orthopaedic Science, 2004, vol. 9, pp. 560-565.

Weisstein, Jason S., M.D. et al.; "Oncologic Approaches to Pediatric Limb Preservation"; Journal of the American Academy of Orthopaedic Surgeons; vol. 13, No. 8, Dec. 2005.

\* cited by examiner

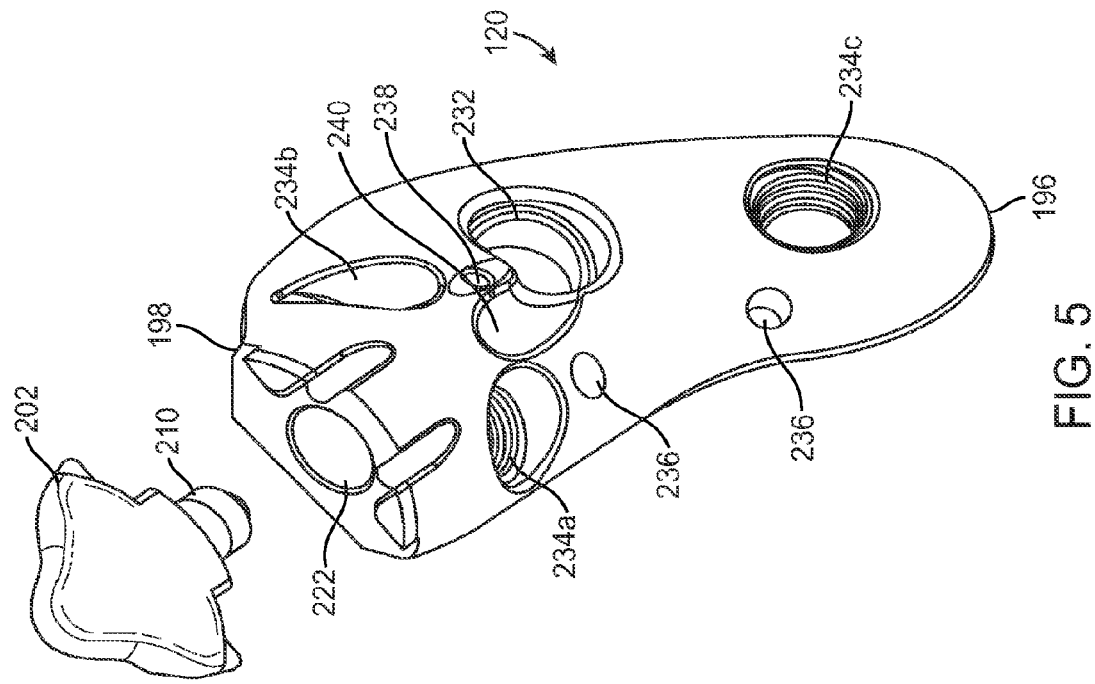
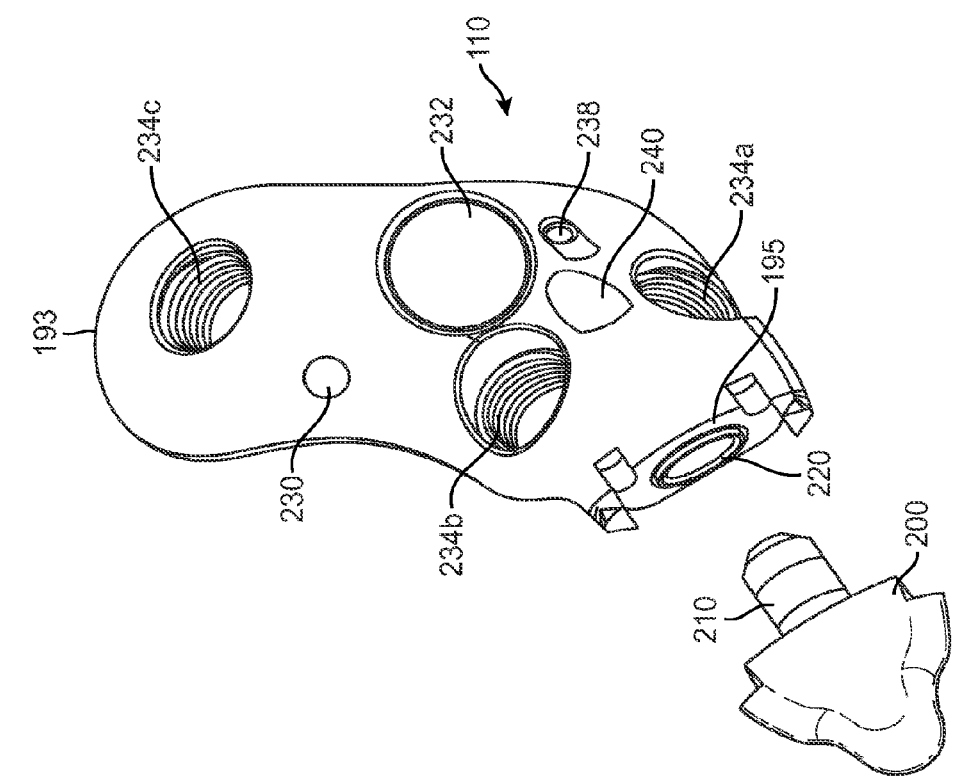

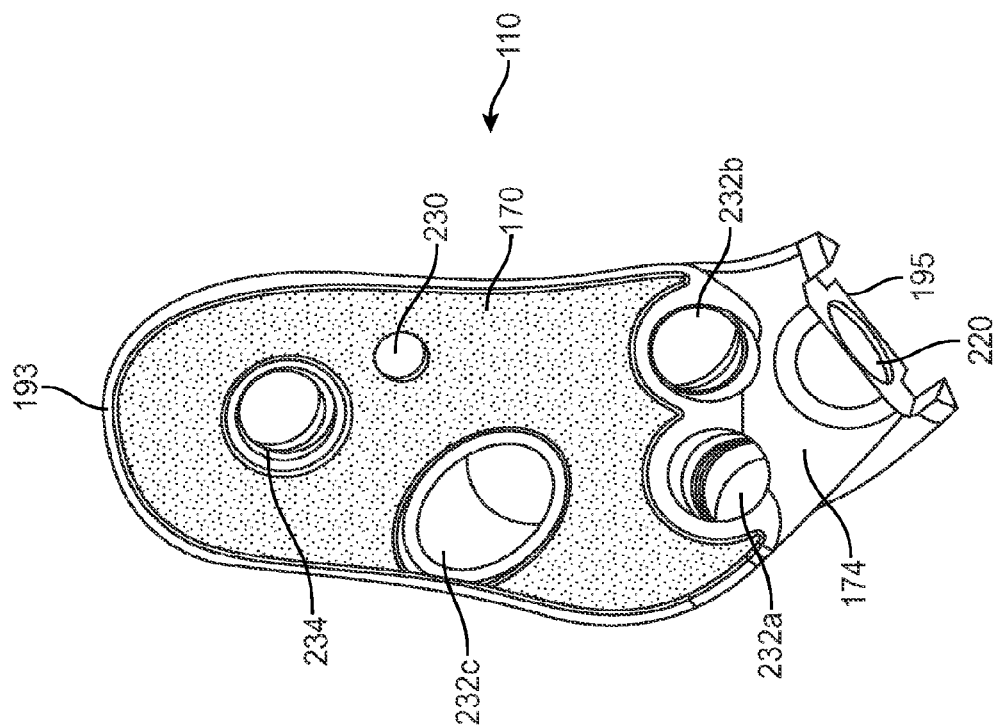
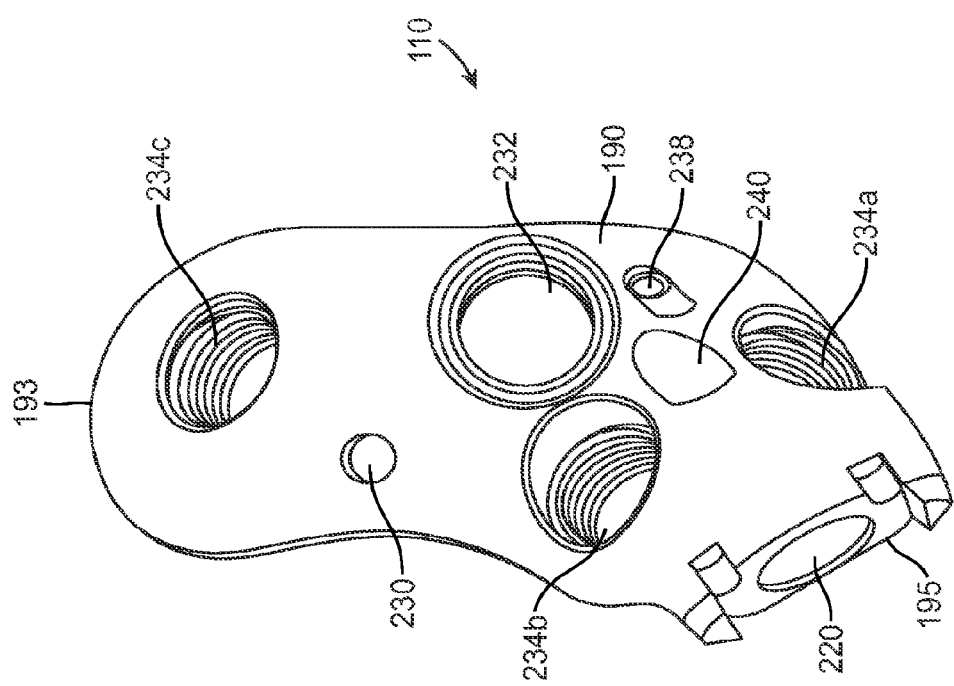

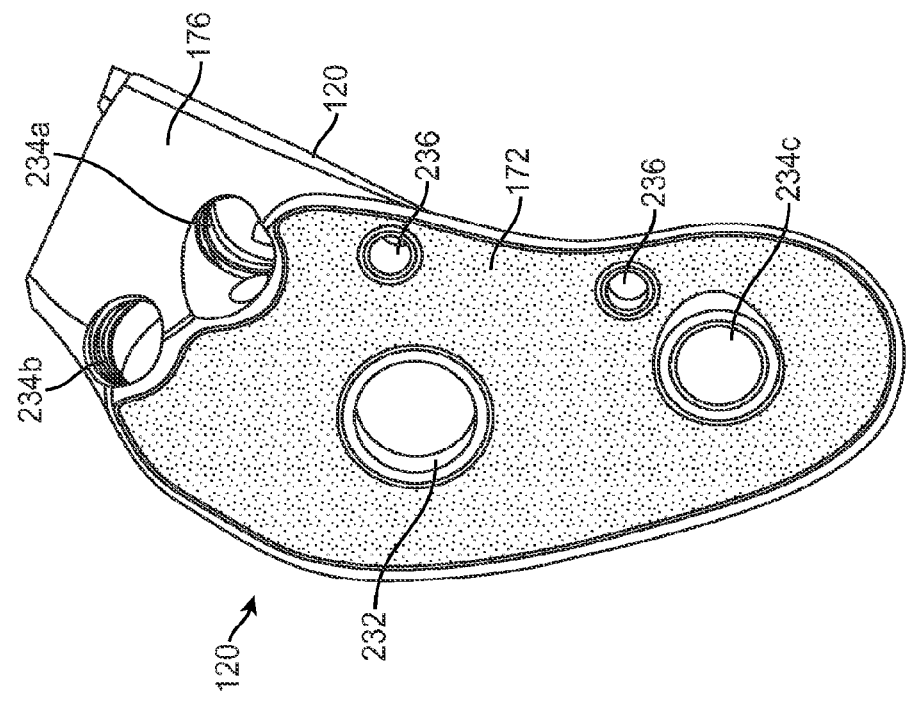
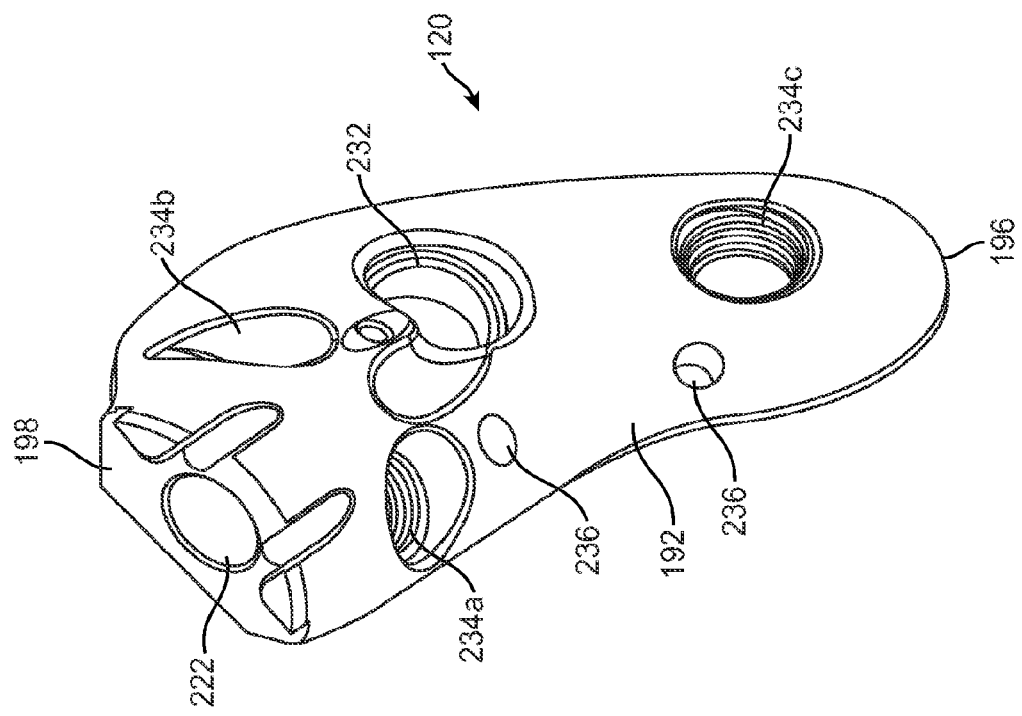
FIG. 8B
FIG. 8A

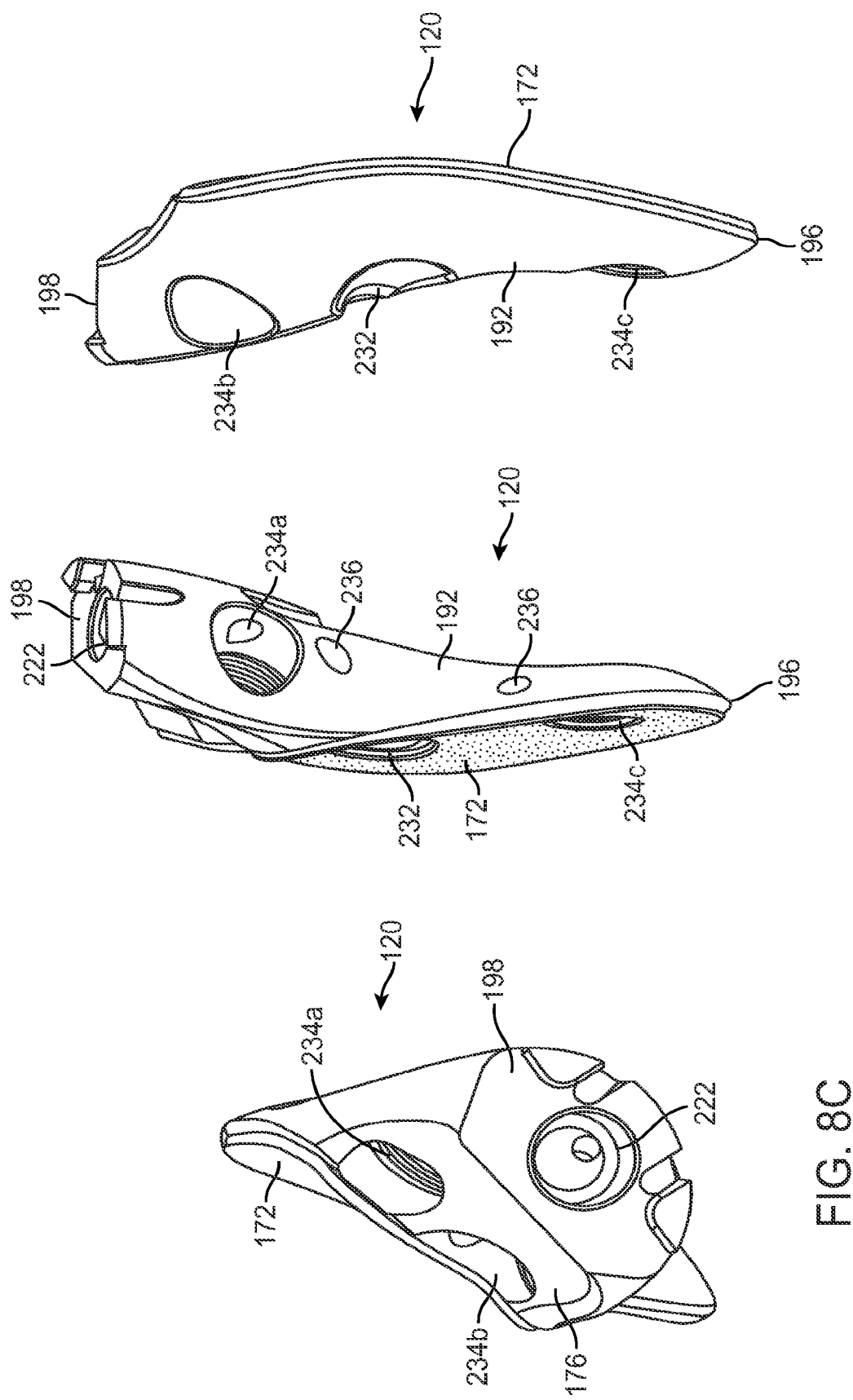

FEMORAL AND TIBIAL BASES

This application is a Divisional of, and claims priority under 35 U.S.C. §120 to, U.S. application Ser. No. 12/755,335, filed 6 Apr. 2010, and is a Continuation-in-Part, and claims priority under 35 U.S.C. §120 to, U.S. application Ser. No. 12/112,442, filed 30 Apr. 2008. U.S. application Ser. No. 12/112,442 is a continuation-in-part of U.S. application Ser. No. 11/743,097, filed 1 May 2007, a continuation-in-part of U.S. application Ser. No. 11/743,605, filed 2 May 2007, a continuation-in-part of U.S. application Ser. No. 11/775,139, filed 9 Jul. 2007, a continuation-in-part of U.S. application Ser. No. 11/775,149, filed 9 Jul. 2007, and a continuation-in-part of U.S. application Ser. No. 11/775,145, filed 9 Jul. 2007. The entireties of all of the foregoing applications are expressly incorporated by reference herein.

BACKGROUND

Various embodiments disclosed herein are directed to structure for attachment to body anatomy, and more particularly, towards approaches for providing mounting members for trans-articular implantable mechanical energy absorbing systems.

Joint replacement is one of the most common and successful operations in modern orthopaedic surgery. It consists of replacing painful, arthritic, worn or diseased parts of a joint with artificial surfaces shaped in such a way as to allow joint movement. Osteoarthritis is a common diagnosis leading to joint replacement. Such joint replacement procedures are a last resort treatment as they are highly invasive and require substantial periods of recovery. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unincompartmental arthroplasty in which the articular surfaces of only one of multiple compartments at a joint (such as the surfaces of the thigh and shin bones on just the inner side or just the outer side at the knee) are replaced.

Arthroplasty, as a general term, is an orthopaedic procedure which surgically alters the natural joint in some way. Arthroplasty includes procedures in which the arthritic or dysfunctional joint surface is replaced with something else as well as procedures which are undertaken to reshape or realigning the joint by osteotomy or some other procedure. A previously popular form of arthroplasty was interpositional arthroplasty in which the joint was surgically altered by insertion of some other tissue like skin, muscle or tendon within the articular space to keep inflammatory surfaces apart. Another less popular arthroplasty is excisional arthroplasty in which articular surfaces are removed leaving scar tissue to fill in the gap. Among other types of arthroplasty are resection(al) arthroplasty, resurfacing arthroplasty, mold arthroplasty, cup arthroplasty, silicone replacement arthroplasty, and osteotomy to affect joint alignment or restore or modify joint congruity.

The most common arthroplasty procedures including joint replacement, osteotomy procedures and other procedures in which the joint surfaces are modified are highly invasive procedures and are characterized by relatively long recovery times. When it is successful, arthroplasty results in new joint surfaces which serve the same function in the joint as did the surfaces that were removed. Any chodrocytes (cells that control the creation and maintenance of articular joint surfaces), however, are either removed as part of the arthroplasty, or left to contend with the resulting new joint anatomy and injury. Because of this, none of these currently available therapies are chondro-protective.

A widely-applied type of osteotomy is one in which bones beside the joint are surgically cut and realigned to improve alignment in the joint. A misalignment due to injury or disease in a joint related to the direction of load can result in an imbalance of forces and pain in the affected joint. The goal of osteotomy is to surgically re-align the bones at a joint such as by cutting and reattaching part of one of the bones to change the joint alignment. This re-alignment relieves pain by equalizing forces across the joint. This can also increase the lifespan of the joint. The surgical realignment of the knee joint by high tibial osteotomy (HTO) (the surgical re-alignment of the upper end of the shin bone (tibia) to address knee malalignment) is an osteotomy procedure done to address osteoarthritis in the knee. When successful, HTO results in a decrease in pain and improved function. However, HTO does not address ligamentous instability—only mechanical alignment. Good early results associated with HTO often deteriorate over time.

Other approaches to treating osteoarthritis involve an analysis of loads which exist at a joint and attempts to correct (generally reduce) these loads. Both cartilage and bone are living tissues that respond and adapt to the loads they experience. Within a nominal range of loading, bone and cartilage remain healthy and viable. If the load falls below the nominal range for extended periods of time, bone and cartilage can become softer and weaker (atrophy). If the load rises above the nominal level for extended periods of time, bone can become stiffer and stronger (hypertrophy). Osteoarthritis or breakdown of cartilage due to wear and tear can also result from overloading. When cartilage breaks down, the bones rub together and cause further damage and pain. Finally, if the load rises too high, then abrupt failure of bone, cartilage and other tissues can result.

The treatment of osteoarthritis and other bone and cartilage conditions is severely hampered when a surgeon is not able to control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain. However, lack of patient compliance and the inability of the devices to facilitate and support the natural motion and function of the diseased joint have been problems with these external braces.

Prior approaches to treating osteoarthritis have also failed to account for all of the basic functions of the various structures of a joint in combination with its unique movement. In addition to addressing the loads and motions at a joint, an ultimately successful approach must also acknowledge the dampening and energy absorption functions of the anatomy. Prior devices designed to reduce the load transferred by the natural joint typically incorporate relatively rigid constructs that are incompressible. Mechanical energy (E) is the action of a force (F) through a distance (s) (i.e., $E=F^{\times}s$). Device constructs which are relatively rigid do not allow substantial energy storage as they do not allow substantial deformations - do not act through substantial distances. For these relatively rigid constructs, energy is transferred rather than stored or absorbed relative to a joint. By contrast, the natural joint is a construct comprised of elements of different compliance characteristics such as bone, cartilage, synovial fluid, muscles, tendons, ligaments, and other tissues. These dynamic elements include relatively compliant ones (ligaments, tendons, fluid, cartilage) which allow for substantial energy absorption and storage, and relatively stiffer ones (bone) that allow for efficient energy transfer. The cartilage in a joint compresses under applied force and the resultant force displacement product represents the energy absorbed by cartilage. The fluid content of cartilage also acts to stiffen its response to load applied quickly and dampen its response to loads applied slowly. In this way, cartilage acts to absorb and store, as well as to dissipate energy.

With the foregoing applications in mind, it has been found to be necessary to develop effective structures for mounting to body anatomy which conform to body anatomy and cooperate with body anatomy to achieve desired load reduction, energy absorption, energy storage, and energy transfer. The structure should also provide a base for attachment of complementary structure across articulating joints.

For these implant structures to function optimally, they should not cause a disturbance to apposing tissue in the body, nor should their function be affected by anatomical tissue. Moreover, there is a need to reliably and durably transfer loads across members defining a joint. Such transfer can only be accomplished where the base structure is securely affixed to anatomy. It has also been found desirable that a base have a smaller bone contact footprint. In this way, a less invasive implantable procedure can be possible, surgical time can be decreased, and larger variations in and greater members of patients can be accommodated with the same base geometries.

Therefore, what is needed is an effective base for connecting an implantable trans-articular assembly and one which does so with a reduced or minimized bone contacting surface area.

SUMMARY

Briefly, and in general terms, the disclosure is directed to bases that are mountable to a bone and may be used for cooperation with an implantable trans-articular system. In one approach, the bases facilitate mounting an extra-articular implantable absorber or mechanical energy absorbing system.

According to one embodiment, the bases of the energy absorbing system are curved to match the bone surfaces of the femur and tibia and are secured with bone screws. In one particular embodiment, the base has a bone contacting surface area of less than 750 mm². In one aspect, the base includes a total of three threaded holes for receiving locking screws. In a further aspect, the base includes a single hole adapted to receive a compression screw and certain bases can further include at least one hole sized to accept a K-wire (Kirschner wire) or Steinmann pin.

In further aspects, the base of the present disclosure contemplates the use of locking screws with threaded heads as well as bases with three threaded holes forming a triangular pattern. In one approach, a non-threaded hole for receiving a compression screw is configured entirely or at least partially within an area defined by the triangle pattern. One contemplated femoral base can include three threaded holes having axes all three with non-parallel trajectories. Additionally, the femoral base can include a K-wire hole having an axis which is substantially parallel to an axis of a non-threaded opening provided for a compression screw. The tibial base can have a hole for a compression screw which is perpendicular to bone. Further, the position and number of locking screw holes of the bases are selected to reduce moment forces on the bases as well as provide an anti-rotation function.

It is also contemplated that various versions of both femoral and tibial bases can be provided so that larger segments of the population can be treated. In one particular approach, three versions of femoral bases can be provided as a kit. Such femoral bases can be characterized by the angle between the plane in which locking screws affixing the femoral base to bone contact the bone and a line perpendicular to the sagittal plane of the patient. In this regard, angles of 40°, 45° and 50° are contemplated.

The various tibial bases which can be provided as a kit and can include 11 mm, 14 mm and 17 mm versions. Such dimensions represent the distance from bone to a center of rotation of a ball and socket arrangement associated with the particular tibial base.

The femoral and tibial bases are also designed to preserve the articulating joint and capsular structures of the knee. Accordingly, various knee procedures, including uni-compartmental and total joint replacement, may be subsequently performed without requiring removal of the bases.

In one specific embodiment, the bases each include a body having an inner surface that is curved in shape to mate with a bone surface. The inner surface contacts the bone surface and may be porous, roughened or etched to promote osteointegration. Osteointegration is a process of bone growth onto and about an implanted device that results in integrating the implant to the bone, thereby facilitating the transfer of load and stress from the implant directly to the bone. The inner surface can be coated with an osteointegration composition. The base is also shaped to avoid and preserve structures of the knee. Moreover, the base is configured to locate a mounting member on the bone in order to position a kinematic load absorber for optimal reduction of forces on a joint. The base is a relatively rigid structure that may be made from metal, polymer or ceramic materials including titanium, cobalt chrome, or polyetheretherketone (PEEK) or a combination thereof. In an alternate approach, the base can be formed at least partially from flexible material.

It is contemplated that the base includes a low-profile body that is generally elongate and includes first and second end portions. The first end terminates in a curved manner and the second end includes structure for mating with a mount for an absorber arrangement. The body is non-planar such that the second end of the body is elevated as compared to the first end of the body. In an application relating to treating a knee joint, the inner surface of the body can be curved so as to be shaped to fit to the medial surface of the femur and/or tibia on opposite sides of a knee joint. The inner surface can also be curved to mate with other surfaces such as lateral surfaces of the femur and tibia.

Other features and advantages will become apparent from the following detailed description, taken in conjunction with the accompanying drawings, which illustrate by way of example, the features of the various embodiments.

BRIEF DESCRIPTION OF THE DRAWINGS

FIG. 4 is an enlarged side view, depicting a femoral base of the system of FIG. 3 with a socket removed;

FIG. 5 is an enlarged side view, depicting a tibial base of the system of FIG. 3 with a socket removed;

FIGS. 6A-6E are various angled views of the femoral base shown in FIG. 4;

FIGS. 8A-E are various coupled views of the tibial base shown in FIG. 5; and

DETAILED DESCRIPTION

Figure 1:
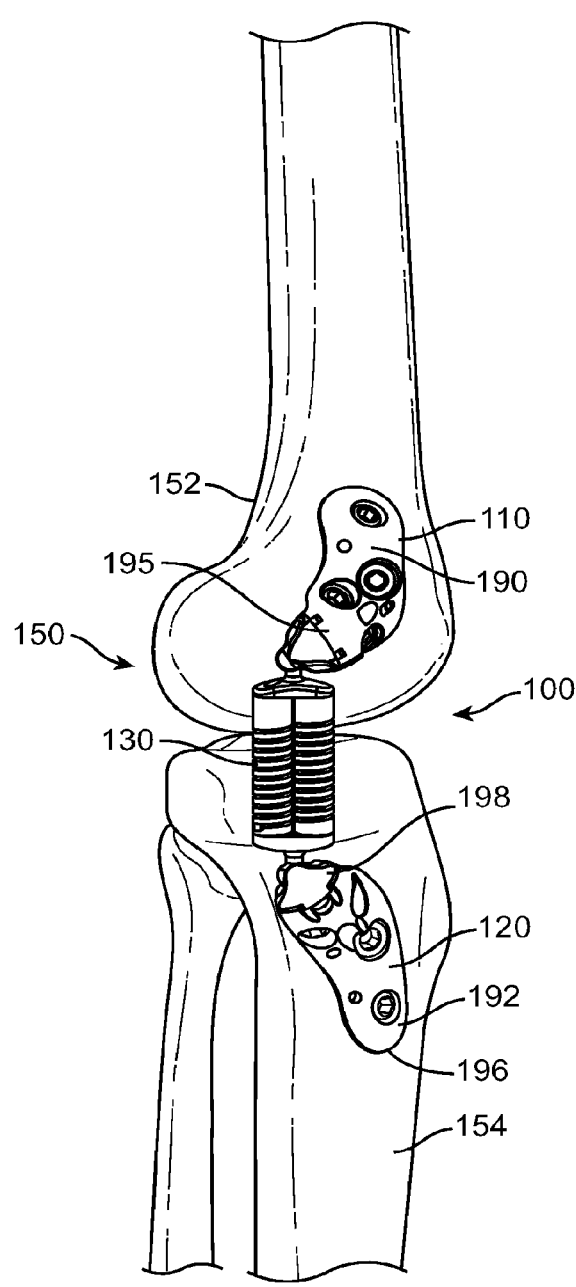
FIG. 1 is a side view, depicting an energy absorbing system attached across a knee joint.

Various embodiments are disclosed which are directed to bases for attachment to body anatomy. In a preferred approach, femoral and tibial bases are provided for attachment of an extra-articular implantable mechanical energy absorbing system to the body anatomy.

In a specific embodiment, the femoral and tibial bases are shaped to match the medial surfaces of the femur and tibia, respectively. The bases have a low-profile design and curved surfaces thereby minimizing the profile of the bases when mounted to the bone surface and enabling atraumatic motion of the adjoining soft tissues over the bases. The bases are secured to bone surfaces with one or more fastening members.

The base can be configured to be an anchor for the extra-articular implantable absorber or mechanical energy absorbing system used to reduce forces on the knee or other joints (e.g., finger, toe, elbow, hip, ankle) The base also can be designed to distribute loads onto the bone from an extra-articular implantable absorber or mechanical energy absorbing system while avoiding articulating joint and capsular structures.

Various shapes of bases are contemplated and described. Moreover, it is contemplated that various sized and similar shaped bases be made available to a physician in a kit so that a proper fit to variably sized and shaped bones can be accomplished. In that regard, it is contemplated that up to three or more different femoral and tibial bases can be available to a physician.

The bases disclosed herein are structures that are different and distinct from bone plates. As defined by the American Academy of Orthopedic Surgeons, bone plates are internal splints that hold fractured ends of bone together. In contrast, the bases disclosed herein are designed to couple to and transfer loads from a absorber of an implanted extra-articular system to the bones of the joint. Furthermore, the loading conditions of a bone plate system are directly proportional to the physiological loads of the bone it is attached to, by contrast the loading conditions of a base is not directly proportional to the physiological loading conditions of the bone but is directly proportional to the loading conditions of the absorber to which it is coupled. In various embodiments, the base is configured to transfer the load through the fastening members used to secure the base to the bone and/or one or more osteointegration areas on the base. The bases are designed and positioned on the bone adjacent a joint to achieve desired kinematics of the absorber when the absorber is attached to the bases.

The approaches to the bases disclosed herein address needs of the anatomy in cyclic loading and in particular, provides an approach which achieves extra-cortical bony in-growth under cyclic loading. In certain disclosed applications, shear strength of about 3 MPa or more can be expected.

Referring now to the drawings, wherein like reference numerals denote like or corresponding parts throughout the drawings and, more particularly to FIGS. 1-9, there are shown various embodiments of a base that may be fixed to a bone. The terms distal and proximal as used herein refer to a location with respect to a center of rotation of the articulating joint.

FIG. 1 illustrates one embodiment of an extra-articular implantable mechanical energy absorbing system 100 as implanted at a knee joint to treat the symptoms of pain and loss of knee motion resulting from osteoarthritis of the medial knee joint. The mechanical energy absorbing system 100 includes femoral and tibial bases 110, 120, respectively. An articulated absorber 130 is connected to both the femoral and tibial bases 110, 120. As shown in FIG. 1, the knee joint is formed at the junction of the femur 152, the tibia 154 and the fibula 156. Through the connections provided by the bases 110, 120, the absorber assembly 130 of the mechanical energy absorbing system 100 can function to absorb and reduce load on the knee joint 150 defined by a femur 152 and a tibia 154. According to one example, the system 100 is placed beneath the skin (not shown) and outside the joint using a minimally invasive approach and resides at the medial aspect of the knee in the subcutaneous tissue. The system 100 requires no bone, cartilage or ligament resection. The only bone removal being the drilling of holes for the screws which quickly heal if screws are removed.

It is also to be recognized that the placement of the bases 110, 120 on the bones without interfering with the articular surfaces of the joint is made such that further procedures, such as a total knee arthroplasty (TKA), unicompartmental knee arthroplasty (UKA) or other arthroplasty procedure, can be conducted at the joint at a later date. For the later procedure, the bases 110, 120 can remain in place after removing the absorber assembly 130 or both the absorber assembly and bases can be removed. Additionally, the absorber assembly 130 can be changed out with a new absorber assembly without having to replace the bases.

The various embodiments of the bases 110, 120 describe herein may be made from a wide range of materials. According to one embodiment, the bases are made from metals, metal alloys, or ceramics such as, but not limited to, Titanium, stainless steel, Cobalt Chrome or combinations thereof. Alternatively, the bases are made from thermo-plastic materials such as, but not limited to, high performance polyketones including polyetheretherketone (PEEK) or a combination of thermo-plastic and other materials. Various embodiments of the bases are relatively rigid structures. Preferably, the material of the base is selected so that base stiffness approximates the bone stiffness adjacent the base to minimize stress shielding.

Figure 2:
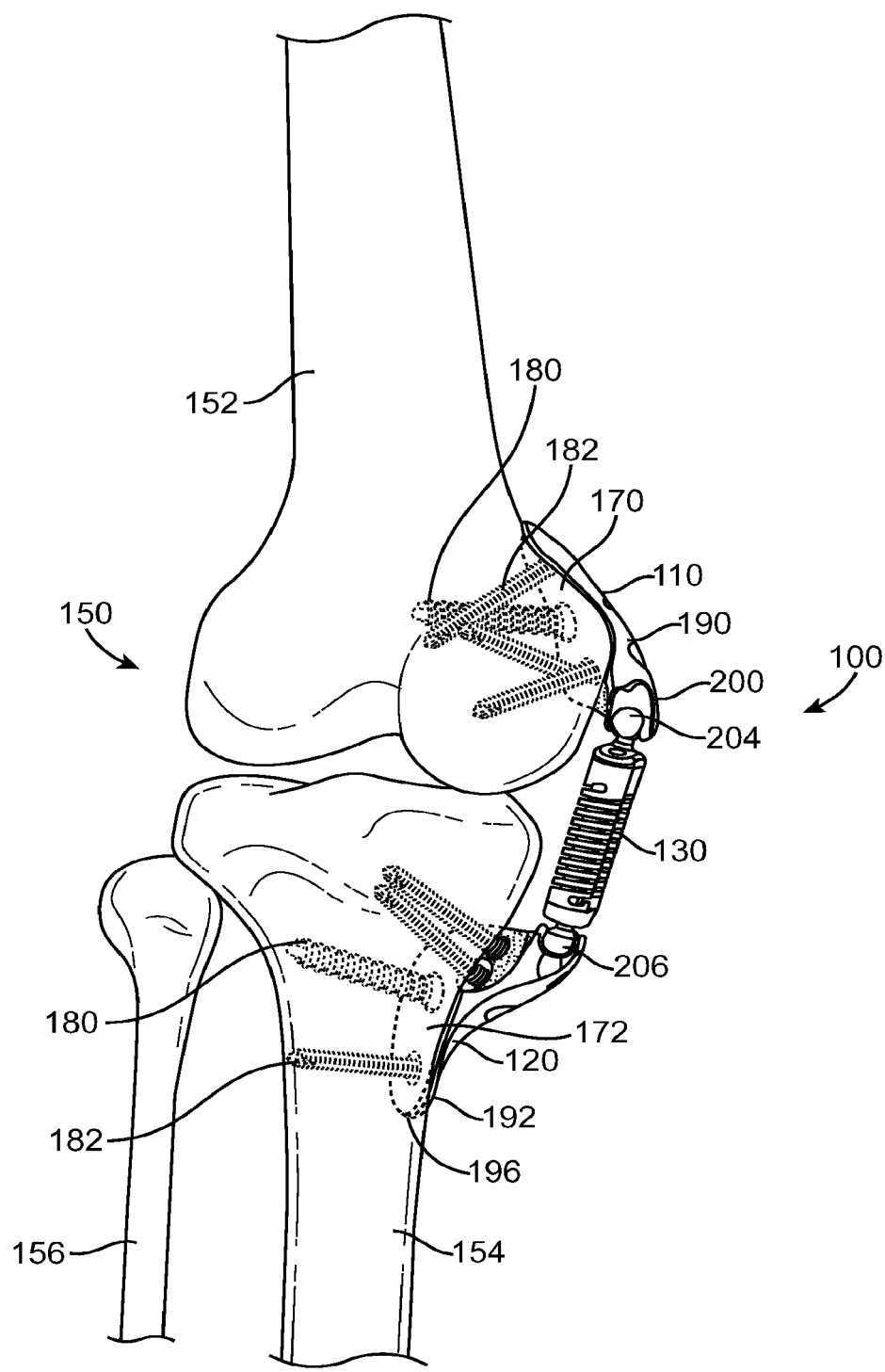
FIG. 2 is a side view, depicting the system of FIG. 1 with the joint anatomy shown in a hidden format.

Turning now to FIG. 2, it can be appreciated that the femoral and tibial bases 110, 120 include various surfaces 170, 172 which are curved to substantially match the surfaces of bones to which they are affixed. Moreover, it is apparent that various affixating structures, such as screws 180, 182, are contemplated for affixing the bases 110, 120 to body anatomy.

With reference to FIG. 2, a femoral base 110 fixable to a medial surface of a femur 152 is illustrated. It is to be recognized, however, that the base 110 can be configured to be fixed to a lateral side of the femur 152 or other anatomy of the body. The femoral base 110 includes an outer surface 190 and an inner surface 170. The outer surface 190 of the base has a low-profile and is curved to eliminate any edges or surfaces that may damage surrounding tissue when the base is affixed to bone. The inner surface 170 and outer surface 190 are not coplanar and serve differing functions which the inner surface conforming to the bone shape and the outer surface providing a smooth transition between the bone and the absorber assembly 130. The proximal end of the outer surface 190 of the femoral base 110 may reside under the vastus medialis and is designed to allow the vastus medialis muscle to glide over the outer surface of the base.

The femoral base 110 is intended to be positioned on the femur at a location that allows the center of knee rotation to be aligned relative to a center of rotation of a femoral articulation, such as the ball and socket joint 204 of the absorber assembly 130. According to one embodiment, the base 110 is mounted to the medial epicondyle of the femur 152 so that a mounting structure 220 (described below) connecting the absorber to the femoral base 110 is located anterior and superior to the center of rotation of the knee. Mounting the absorber 130 at this location allows the extra-articular mechanical energy absorbing system 100 to reduce forces during the "stance" or weight bearing phase of gait between heal strike and toe-off. Alternatively, the femoral base may be mounted at different positions on the femur to reduce forces during different phases of a person's gait.

Figure 3:
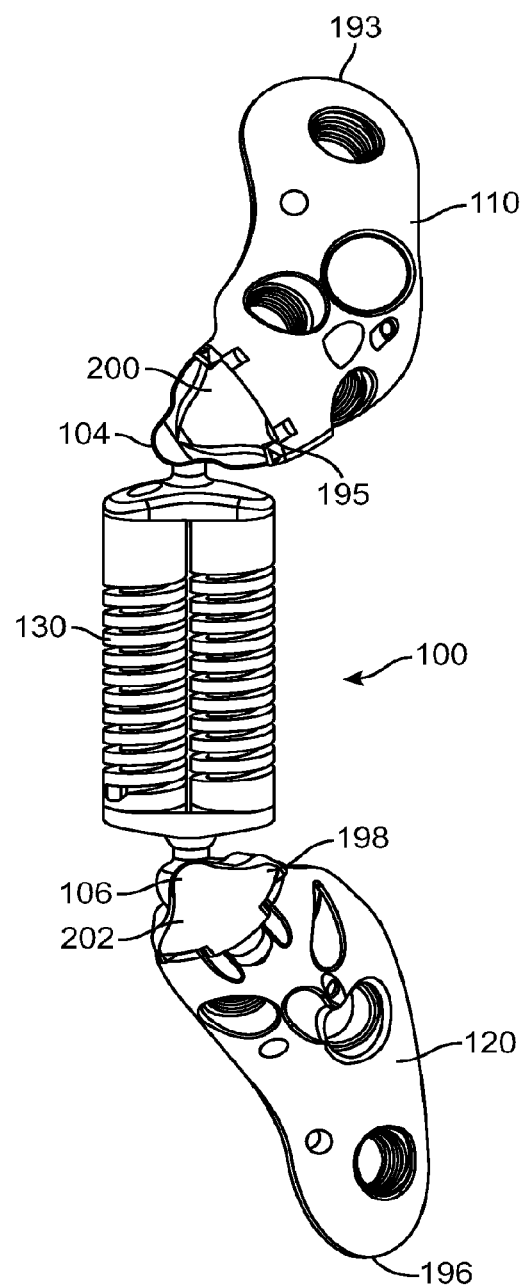
FIG. 3 is an enlarged side view, depicting the system of FIG. 1 removed from anatomy.

As shown in FIG. 3, the femoral base 110 is generally elongate and includes a first curved end 193 and a second squared mounting end 195 which is raised to suspend the absorber 130 off the bone surface to avoid contact between the absorber and the knee capsule and associated structures of the knee joint. The body of the base 110 includes a curved portion and the squared second end 195 is at an angle with respect to the first end 193. It is contemplated that the absorber 130 be offset approximately 2-15 mm from the surface of the joint capsule. In one specific embodiment, the entire second end 195 which is connectable with an associated socket structure 200 is offset from the capsular structure of the knee. Thus, the system 100 is extra-articular or outside of the capsular structure of the knee. The system 100 is also trans-articular or extends across the articular structure of the joint. In one embodiment, the second end 195 is designed to be located offset approximately 3 mm from the capsular structure. In another approach, the offset is approximately 6 mm from the capsular structure. Accordingly, the base 110 allows for positioning of an extra-articular device on the knee joint while preserving the knee structures including the anterior cruciate ligament (ACL), posterior cruciate ligament (PCL), Pes anserius tendon, and allowing future surgical procedures such as TKA or UKA.

Also shown in FIG. 2 is an embodiment of a tibial base 120 that is mountable to the medial surface of the tibia 154. As shown, the tibial base 120 has an overall elongate shape and a curved portion end portion. An outer surface of the body 192 is curved convexly where the center of the body is thicker than the edges of the body. The tibial base 120 also includes rounded edges in order to minimize sharp edges that may otherwise cause damage to surrounding tissues when the base is coupled to the tibia 154. The body includes a rounded first end 196 and a squared-off second end 198 which defines an angle with respect to the elongate portion of the body. In various embodiments, the second end 198 is configured to be spaced from bone as well as attach to the absorber 130. The underside 172 of the body is the portion of the tibial base 120 that contacts the tibia. The squared off end 198 is offset medially from the bone.

As best seen in FIGS. 3-5, the squared off second ends 195, 198 of the femoral 110 and tibial 120 bases are shaped to mate with socket structures 200, 202. In one approach, the sockets 200, 202 each include a post 210 which is press fit into a corresponding bore 220, 222 formed in the squared off ends of the bases 110, 120. The sockets 200, 202, in turn, receive ball structures forming ends of the absorber 130, as shown most clearly in FIG. 2.

As shown most clearly in FIGS. 6B and 8B, it is contemplated that the inner surfaces 170, 172 of the bases 110, 120 can include bone contacting surfaces 170, 172 shaped to match and directly contact the bone surface as well as curved offset surfaces 174, 176 between the bone contacting surfaces and the squared off mounting ends 195, 198. These inner curved offset surfaces 174, 176 are designed to not come into contact with bone and to provide an offset of the tibia articulation, such as the ball and socket joints 204, 206, in the medial direction from the joint. The inner bone contacting surfaces 170, 172 may be curved in an anterior to posterior direction as well as superior to inferior directions to conform to the shape of the typical patient femur. According to one embodiment, the inner bone contacting surfaces 170, 172 includes one or more compositions that induce osteointegration to the cortex of long bones in the body. Additionally or alternatively, the inner bone contacting surfaces 170, 172 can be roughened or etched to improve osteointegration. The inner bone contacting surfaces of the bases 110, 120 conform to the bone surface area. The amount of bone contacting surface area can vary depending on the load. In the illustrated example, the amount of bone contacting surface area provided in able to support expected shear forces resulting from 60 lbs of load as well as to counter bending moments and tensile forces on the bases tending to lift the bases from the bone. The surface area of the bone contacting surface 170 provided by the femoral and tibial bases 110, 120 is significantly less than other bases due to the improved fit and improved fixation provided by the new base shape and improved screw arrangement. For osteointegration the bone contacting surface area desired for a base is determined based on the amount of load on the absorber and the calculated shear strength of the interfaces between the bone and the base. For example, the surface area of the inner bone contacting surface 170 of the femoral base 120 is less than 650 mm$^2$, preferably less thank 500 mm$^2$, for secure fixation to the femur and is capable of carrying 60 pounds in 4 mm of compression of a kinematic load absorber 130. A safety factor may be built into base as larger surfaces may be used in other embodiments. For example, a femoral base can include an osteointegration surface area of approximately 350 mm$^2$. Since a limited number of base shapes and sizes are generally available to a surgeon, a perfect fit of a base to a bone is not always achieved. With a smaller base size, an adequate fit can be achieved with a reduced number of bases because there is less surface area to be matched with bone shape. In this way the same number of bases are also able to accommodate a larger selection of patient anatomies.

Although the use of compression screws are described herein, the methods and systems described can be employed without the use of a compression screw and may use the alternative of an instrument designed for delivering compression while locking screws are placed.

For a tibial base 120 for secure fixation to the femur and capability of carrying 60 pounds in 4 mm of compression of a kinematic load absorber 130, the bone contacting inner surface 172 is less than 750 mm$^2$, preferably less than 700 mm$^2$ for secure fixation to the tibia.

In certain embodiments, the load transferred from the absorber to the base can change over time. For example, when the base is initially fixed to the bone, the fastening members carry all the load. Over time, as the base may become osteointegrated with the underlying bone at which time both the fastening members and the osteointegrated surface carry the load from the implanted system. The loading of the bases also varies throughout motion of the joint as a function of the flexion angle and based on patient activity.

The femoral and tibial bases 110, 120 include a plurality of openings that are sized to receive fastening members used to permanently secure the base to the bone. The openings define through-holes that may receive fastening members such as compression screws and/or locking screws. The openings may have divergent bore trajectories to further maximize the pull forces required to remove the base from the bone. Although divergent bore trajectories are shown, converging trajectories may also be used as long as interference between the screws is avoided. The number and trajectories of the openings may be varied in alternate embodiments.

As shown in FIGS. 6A-6E, the femoral base 110 includes a plurality of openings 230a, 230b, 232, 234a, 234b and 234c. Openings 230a, 230b have a diameter sized to receive standard K-wires or Steinmann pins that are used to temporarily locate the base 110 on the bone. Openings 232 and 234a-c are sized to receive fastening members used to permanently secure the base 110 to the bone. Opening 232 defines a through hole for a compression screw 180, such as a cancellous bone screws. The compression screw generates compression of bone underneath the base. Openings 234a-c are configured to receive locking screws 182 (see FIG. 2). The locking screws 182 can include a threaded head that engages threaded locking screw holes 234a-c and generally do not provide the bone compression that a compression screw does. Although locking screws with threaded heads and corresponding threaded openings have been described, other types of locking screws are also know having heads that are locked to the base in a manner other than by threading, such as by a sliding lock on the base or an insertable locking member. In one embodiment, the locking screw openings 234a-c are threaded and the K-wire holes 230 and compression screw opening 232 are non-threaded. The K-wire hole 230a has a trajectory or axis parallel to that of the compression screw hole 232. As shown, two of the locking screw openings 234a, 234b are located near the square mounting end 195 of the femoral base 110 in order to receive fasteners which securely fix the base to the bone and maximize resistance to pull-out forces and other forces which might tend to loosen the fasteners. A third locking screw hole 234c is spaced from the other two and closer to the first end 193 of the base 110. The position of the three locking screw holes 234a-c in a triangular arrangement on the base 110 functions to maximize bone quality at the fastener locations and reduce both moments and forces on the base which might cause the base or the fasteners to loosen.

The various energy absorbing devices in the present application are shown without a protective covering or sheath but it is contemplated that they can be within a protective covering or sheath to protect the moving elements from impingement by surrounding tissues and to prevent the devices from damaging surrounding tissue. The bases 110, 120 may be provided with attachment means such as holes 238 for receiving a fastener to attach the sheath to the bases.

The compression screw hole 232 is positioned generally at a center of the femoral base 110 and at least partially within a triangle formed by the locking screw holes 234a-c. It is contemplated that the compression screw hole 232 be unthreaded and is the first hole to receive a fastening structure in the form of the compression screw 180 so as to pull the base 110 tightly against bone. Once the femoral base 110 is so configured against bone, the locking screws 182 are employed to fix the base 110 in place. Each of the locking screw holes 234a-c are oriented in inwardly converging, non-parallel trajectories (i.e. each of the locking screws 182 has a trajectory converging in the direction of insertion with each of the other locking screws) to add strength to the fixation to bone. The parallel trajectories of the K-wire hole 230 and compression screw hole 232 reduce or eliminate displacement of the base 110 during initial fixation by the compression screw 235. The parallel trajectory of the K-wire hole 230 also substantially eliminates the occurrence of binding of the K-wire in the hole after screw fixation. Further, the third locking screw hole 234c positioned near the first end 193 of the base 110 operates to provide an anti-rotation feature. The openings 234a-c may also have divergent bore trajectories to further maximize the pull forces required to remove the base from the bone. The number and trajectories of the openings may be varied in alternate embodiments.

The femoral base 110 can also be provided with a post access port 240 positioned near the squared, mounting end 193 of the base 110. The post access port 240 is sized to receive a tool (not shown) that allows for locking of a socket member 240 (See FIG. 4) to the base 110 by pulling the post 210 of the socket member 240 into the base 110. It is to be further recognized that the openings 232, 234a-c can be countersunk to allow the fastening members to sit below the surface of the base body as shown in FIG. 2. In one specific approach, the openings 232, 234a-c are sized to accommodate 4.0 mm screws. In other approaches, the openings may be sized to accommodate 3.5 mm, 4.5 mm, 5.0 mm, or 6.5 screws.

FIG. 6B illustrates a view of the inner surface 170 of the femoral base 110. The inner surface bone contacting surface 170 can be roughened or etched to improve osteointegration. Alternatively, the inner surface bone contacting surface 170 can be modified in other ways to induce bone growth. In one example, the inner surface bone contacting 170 may be coated with bone morphogenic protein 2 (BMP-2), hydroxyapatite (HA), titanium, cobalt chrome beads, any other osteogenerating substance or a combination of two or more coatings. According to one embodiment, a titanium plasma spray coating having a thickness of approximately 0.025 in.±0.005 in. is applied to the inner bone contacting surface 170. In another embodiment, a HA plasma spray having a thickness of approximately 35 μm±10 μm is applied to facilitate osteointegration. The portions of the inner surfaces of the base which are not in contact with the bone including the curved offset surfaces 174 of the bases may or may not be treated in the same manner to improve osteointegration at the bone contacting surface.

Figure 6C:
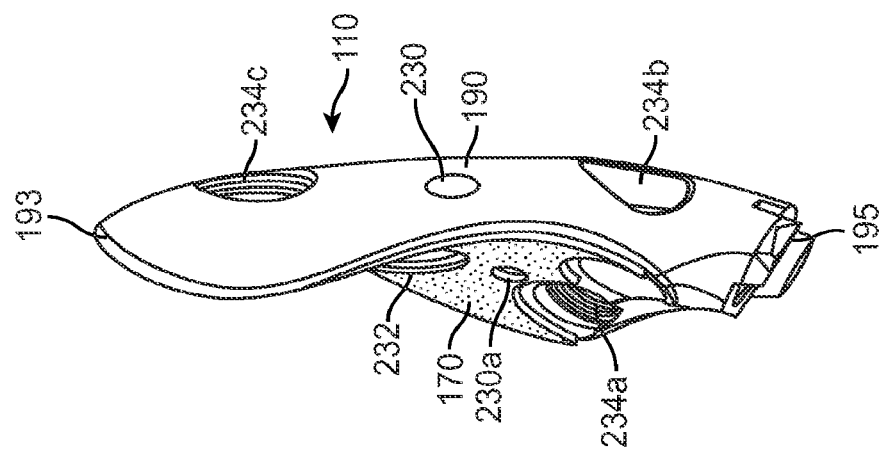
Figure 6D:
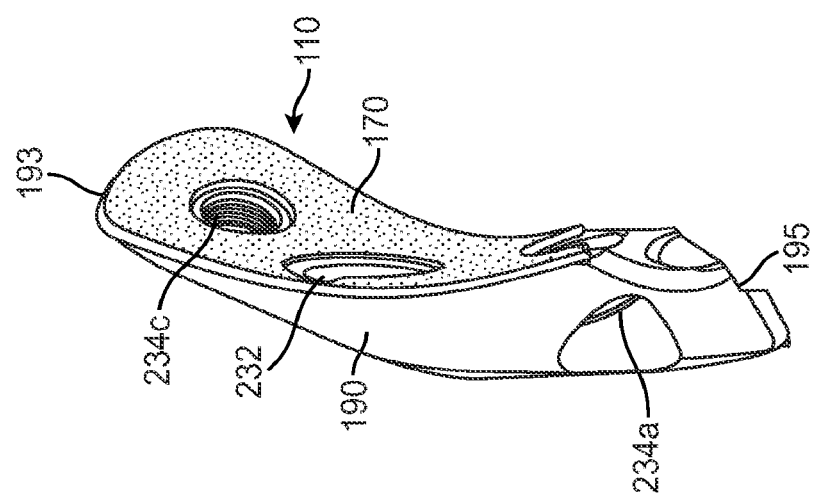
Figure 6E:
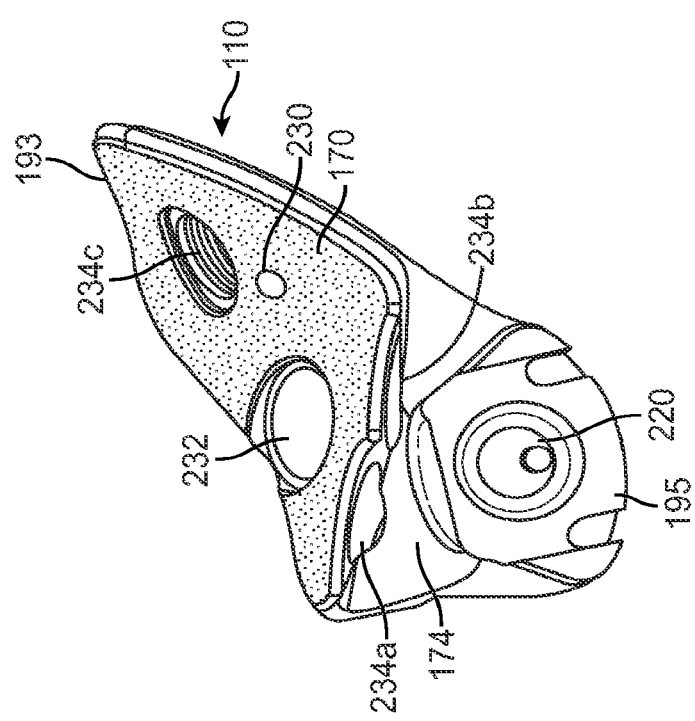
Figure 7:
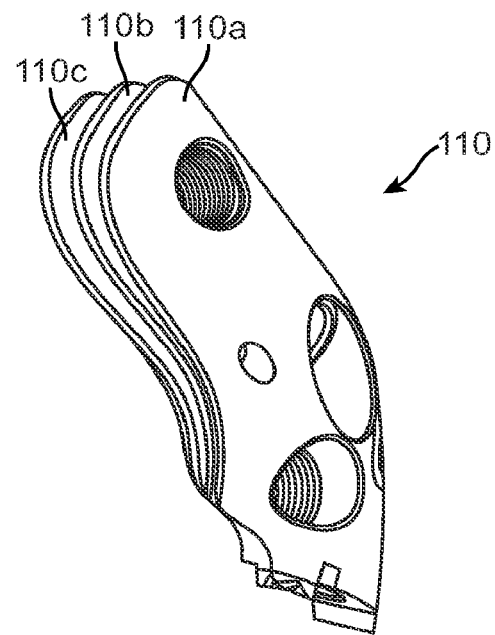
FIG. 7 is a perspective view, depicting three embodiments of a femoral base.
Figure 9:
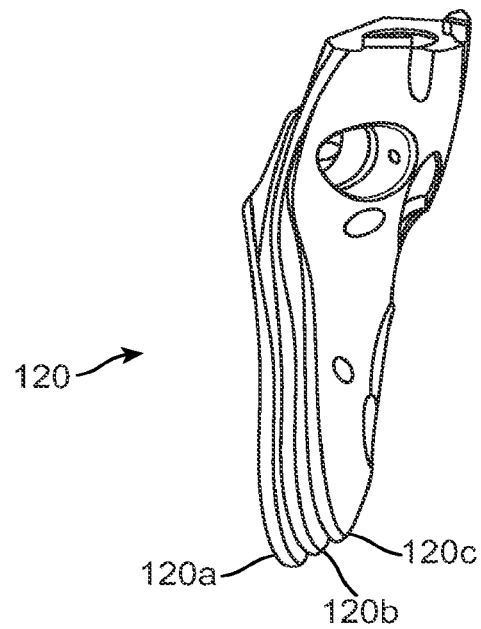
FIG. 9 is a perspective view, depicting three embodiments of a tibial base.

As shown in FIGS. 6C-6E, the inner surface 170 has a first radius of curvature at the first end 193 of the base 110 and a second radius of curvature at the second end 195 of the inner surface 170, where the first radius of curvature can differ from the second radius of curvature. Additionally, the inner surface 170 is generally helical in shape when moving from the first end 193 to the second end 195 of the base 110. That is, the inner surface 170 twists when moving from the top of the inner surface to the bottom of the inner surface. The helical nature of the inner surface 170 generally follows the shape of the distal medial femur when moving distally (down the femur) and posteriorly (front to back). Accordingly, the curved shape of the inner surface 170 helps to reduce the overall profile of the base 110 when affixed to the medial surface of the femur. Additionally, the matching curved shape of the inner surface 28 increases the surface area in which the femoral base 110 contacts the femur thereby improving load distribution. The curved shape of the outer surface 190 softens the transitions between the absorber 130 and the femoral base 110, between the base and bone, and improves the smooth motion of skin, muscle, and other anatomy over the base.

It is contemplated that femoral base 110 can be provided in two or more versions to accommodate patient anatomies. The two or more versions of the femoral base 110 form a set of bases of different shapes and/or sizes which are modular in that any one of these bases can be used with the same absorber. In one example, three base shapes are provided and designated 40°, 45°, 50° bases 110a, 110b, 110c (See FIG. 7). These angles represent the angle between a plane formed by the three points where the locking screws 234 contact the bone and a line perpendicular to the saggital plane (vertical A-P plane through the joint) of the patient. The femoral bases 110 are substantially the same size and shape, but are each rotated by 5 degrees about the center of rotation of a ball and socket joint attached to the base (See FIGS. 1 and 2). Such femoral base versions allow improved kinematics by allowing the base to be selected and placed for each particular patient in order to achieve a desired location of the center of rotation. The location of the center of rotation of the ball and socket joint 204 at a desired location allows improved range of motion and desired kinematics for different patient bone geometries. The orientation of the mounting end 195 at a desired orientation is also important to allowing desired kinematics. Placing the femoral ball and socket joint 204 at the desired location and orientation allows controlled clearance between the bone and the absorber 130 during full range of motion, as well as full range of motion of the knee without impingement of the absorber on the socket. In one example, the desired location of the center of rotation of the femoral ball and socket joint 204 is slightly anterior and distal to the radiographic center of rotation of the knee joint. A center of rotation of the knee joint can be approximated by locating the midpoint of Blumensatt's line. The center of rotation of the femoral ball and socket joint can also be arranged to be located at a desired offset distance from the bone. This offset distance is about 2 to 15 mm, preferably about 5 to 12 mm.

The implantable mechanical energy absorbing systems described herein have a total of 7 degrees of freedom including two universal joints each having three degrees of freedom and the absorber having one degree of freedom. However, other combinations of joints may be used to form an implantable energy absorbing system, such as a system having 5 or 6 degrees of freedom.

The figures have illustrated the implantable mechanical energy absorbing systems designed for placement on the medial side of the left knee. It is to be appreciated that a mirror image of the femoral base 110 would be fixable to the medial surface of the right femur for the purposes of unloading or reducing a load on the medial compartment of the knee. In an alternate embodiment, the femoral and tibial bases 110, 120 and the absorber 130 may be configured to be fixed to the lateral surfaces of the left or right femur and to reduce loads on the lateral compartment of the knee. In yet another approach, implantable mechanical energy absorbing systems can be fixed to both the lateral and medial surfaces of the left or right knee joint or of other joints.

As shown in FIGS. 8A-8E, the tibial base 120 also includes a plurality of through holes 232, 234a-c, 236. A non-threaded hole 232 is sized to receive a compression screw 180 (See FIG. 2) and three threaded holes 234a-c are designed to accept locking screws 182. The compression screw hole 232 is positioned generally at a center of the tibial base 120 and at least partially within a triangle formed by the locking screw holes 234a-c. The three openings 234a-c are oriented to provide differing trajectories for fastening members that maximize pull out forces thereby minimizing the possibility that the tibial base 120 is separated from the bone. According to one embodiment, the trajectories of the locking screws 182 in the tibial base 120 are oriented such that the hole trajectories (axes) and corresponding locking screws are normal or approximately normal to the shear loading forces on the base or normal to be surface of the adjacent bone. The screw trajectories are designed to minimize potential for violation of the joint space and/or posterior joint structures.

As with the femoral base, the openings 232, 234a-c can be countersunk to allow the heads of fastening members to sit below the surface of the body as shown in FIG. 2. According to one embodiment, the openings 232, 234a-c are sized to accommodate 4.0 mm diameter fastening members. In other embodiments, the openings 232, 234 may be sized to accommodate 3.5 mm, 4.5 mm, 5.0 mm or other diameter fastening members.

According to one embodiment, a femoral base 110 is implanted by selecting a base which most closely accommodates the patients bone while locating the femoral ball and socket articulation at a desired location, placing the base on the bone, inserting a K-wire through the opening 230a to hold the desired location, inserting the compression screw 180 followed by inserting the locking screws 182. The selection of the best femoral and tibial bases 110, 120 can be accomplished by radiographic assessment, by providing multiple trials of the different bases for manual testing, by providing a base template which represents multiple bases, or by a combination of these or other methods.

While screws are used to fix the femoral and tibial bases 110, 120 to the bone, those skilled in the art will appreciate that any fastening members known or developed in the art may be used in addition to or as an alternative to screw fixation to accomplish desired affixation. Additional instruments and methods which are usable with the bases are described in detail in U.S. Patent Application No. 61/259,052 entitled, "Positioning Systems and Methods for Implanting an Energy Absorbing System," which is incorporated herein by reference in its entirety.

The tibial base 120 may also include a plurality of holes 236 that may be used during alignment of the base 120 on the tibia and sized to receive structures such as a K-wire. Optionally, the base 120 may include a plurality of holes, teeth or other surface features (not shown) to promote bone in-growth thereby improving base stability.

As best seen in FIGS. 8B-8E, the inner bone contacting surface 172 of the tibial base 120 represents the base to bone surface required to support expected shear forces resulting from 60 lbs of load carrying as well as other forces on the base. The inner bone contacting surface 172 can be a roughened surface for improving osteointegration. Alternatively or additionally, the inner surface 172 can be coated to induce bone growth. For example, the inner surface 172 may be coated with bone morphogenic protein 2 (BMP-2) or hydroxyapatite, titanium, cobalt chrome beads. The inner bone contacting surface 172 is a curved surface that matches the tibia shape and promotes good contact between the base 120 and the tibia. Accordingly, the inner surface facilitates the tibial base 120 absorbing and transferring load forces from the base to the tibia. The portions of the inner surfaces of the tibial base 120 which are not in contact with the bone including the curved offset surfaces 176 of the bases may or may not be treated in the same manner as the bone contacting surfaces 172 to improve osteointegration at the bone contacting surface.

The tibial base 120 has a generally low-profile when mounted to the bone. The base 120 is mounted to the medial surface of the tibia in order to preserve critical anatomy such as, but not limited to, medial collateral ligaments. The tibial base shape is designed to remain on an anteriomedial surface of the tibia and to avoid important anatomical structures on the posterior aspect of the tibia.

As best seen in FIG. 2, the second end 198 of the base 120 is offset from the surface of the tibia allowing the absorber to move throughout a range of motion while avoiding anatomical structures and maintaining a low profile of the base. Together the tibial and femoral bases 120, 110 are configured to receive the absorber in a position where the absorber plane is substantially parallel to a line connecting the medial aspects of the femoral and tibial condyles.

The tibial base 120 shown in the figures is configured to be fixed to the medial surface of the left tibia. As those skilled in the art will appreciate, a mirror image of the base 120 would be fixable to the medial surface of the right tibia. Tibial bases 120 can be provided in two or more versions to fit the different anatomy of patients. The two or more versions of the tibial base 120 form a set of bases of different shapes and/or sizes which are modular in that any one of these bases can be used with the same absorber. In one example, three versions 11 mm base 120a, 14 mm base 120b and 17 mm base 120c (See FIG. 9) are provided. These dimension identifiers represent the distance from the tibia to the center of rotation of a tibial ball and socket 206 attached to the tibial base 120 (See also FIGS. 1 and 2). The tibial bases 120 are substantially the same size and shape, but are each translated by 3 mm above the bone to form the three different versions. The new base versions allow improved kinematics by allowing bases to be placed in order to achieve a desired location of the center of rotation. The desired center of rotation of the tibial ball and socket joint 206 is selected to provide controlled clearance between the absorber and the anatomical joint and to prevent impingement of the absorber on the socket.

According to one embodiment, a tibial base 120 is implanted by first selecting a base which most closely accommodates the patient's bone and joint anatomy. To do this, the tibial base is positioned a set distance from the femoral base with the distance there between being defined by the absorber length. Variation of this distance may occur based on absorber compression and patient activity. Once the tibial base 120 is located on the tibia one or more K-wires, compression screws 180 and/or locking screws 182 are inserted in a manner similar to the method used to secure the femoral base 110.

In one specific application, the femoral and tibial bases 110, 120 are designed to have a relatively small footprint which results in a less invasive procedure with smaller incisions needed to implant the bases. The small bases also require less periosteum elevation during surgery resulting in a less invasive procedure. Surgical time can also be shortened by using smaller bases and associated less dissection time and involving fewer screws to insert. In addition to improving the implantation procedure, the smaller bases accommodate larger variations in patient anatomies and accommodate larger numbers of patients with the same number of base versions. This improved fit of bases is the direct result of the fact that there is less surface area that needs to fit closely to the bone.

The use of a single central compression screw combined with surrounding locking screws for fixation allows fixation to be provided nearly entirely by the screws and very little osteointegration of base to bone may be needed. Thus, improved screw fixation is a key to fixation in place of increase surface area.

Although the mechanical energy absorbing system 100 has been illustrated as used to reduce loading on the medial knee, it may also be used in the lateral knee as well as other joints such as the finger, hand, toe, spine, elbow, hip and ankle Other base configurations and shapes which may be suitable for use in some of these applications include those disclosed in U.S. Patent Publication No. 2008/0275562 which is incorporated herein by reference in its entirety.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims. In that regard, various features from certain of the disclosed embodiments can be incorporated into other of the disclosed embodiments to provide desired structure.

We claim:

1. A mechanical energy absorbing system, the system comprising:
   a femoral base configured for implantation on a medial aspect of the femur;
   a tibial base configured for implantation on a medial aspect of the tibia;
   an absorber configured to be connected to the femoral base and the tibial base in an position where the absorber is located in an absorber plane;
   wherein the bases are configured to receive the absorber in a position where the absorber plane is substantially parallel to a line connecting the medial aspects of the femoral and tibial condyles
   wherein the femoral base has a bone contacting surface with a surface area of less than 650 mm$^2$, a single non-threaded opening configured to receive a compression screw, and a plurality of threaded openings configured to receive a plurality of locking screws with threaded locking heads;
   wherein the tibial base has a bone contacting surface area of less than 750 mm$^2$;
   wherein said threaded openings are positioned at three points of a triangle; and
   wherein the non-threaded opening is positioned at least partially within the triangle.

2. The system of claim 1, wherein the tibial base has a single non-threaded opening therein configured to receive a compression screw and a plurality of threaded openings therein configured to receive a plurality of locking screws with threaded locking heads.

3. The system of claim 2, wherein said threaded openings of the tibial base are positioned at three points of a triangle and the non-threaded opening is positioned at least partially within the triangle.

4. The system of claim 2, wherein two of the threaded openings of the tibial base closest to the absorber have axes which cross each other on a bone contacting side of the tibial base.

5. The system of claim 2, wherein a threaded opening of the tibial base furthest from the absorber has an axis which does not cross with the axes of the other two threaded openings.

6. A mechanical energy absorbing system, the system comprising:
   a femoral base configured for implantation on a medial aspect of the femur;
   a tibial base configured for implantation on a medial aspect of the tibia;

an absorber configured to be connected to the femoral base and the tibial base in an position where the absorber is located in an absorber plane;

wherein the bases are configured to receive the absorber in a position where the absorber plane is substantially parallel to a line connecting the medial aspects of the femoral and tibial condyles;

wherein the femoral base has a bone contacting surface with a surface area of less than 650 mm$^2$, a single non-threaded opening configured to receive a compression screw, and a plurality of threaded openings configured to receive a plurality of locking screws with threaded locking heads;

wherein the tibial base has a bone contacting surface area of less than 750 mm$^2$; and wherein the femoral base has only three threaded openings therein.

7. The system of claim 6, wherein the tibial base has a single non-threaded opening therein configured to receive a compression screw and a plurality of threaded openings therein configured to receive a plurality of locking screws with threaded locking heads.

8. The system of claim 7, wherein said threaded openings of the tibial base are positioned at three points of a triangle and the non-threaded opening is positioned at least partially within the triangle.

9. The system of claim 8, wherein two of the threaded openings of the tibial base closest to the absorber have axes which cross each other on a bone contacting side of the tibial base.

10. The system of claim 8, wherein a threaded opening of the tibial base furthest from the absorber has an axis which does not cross with the axes of the other two threaded openings.

11. The system of claim 6, wherein the three threaded openings each have axes which cross each other on a bone contacting side of the femoral base.

12. The system of claim 6, wherein bases are configured to receive the absorber at a location offset from the line connecting the medial aspects of the femoral and tibial condyles by 2-15 mm.

* * * * *